United States Patent [19]

Cloutier

[11] 4,207,627
[45] Jun. 17, 1980

[54] KNEE PROSTHESIS

[76] Inventor: Jean-Marie Cloutier, 12 Aberdeen, Westmount, Quebec, Canada, H3Y 3A4

[21] Appl. No.: 4,556

[22] Filed: Jan. 18, 1979

[51] Int. Cl.² ............................................. A61F 1/24
[52] U.S. Cl. .................... 3/1.911; 128/92 C
[58] Field of Search .................. 3/1.9–1.911; 128/92 C

[56] References Cited

U.S. PATENT DOCUMENTS

| | | | |
|---|---|---|---|
| 3,813,700 | 6/1974 | Tavernetti et al. | 3/1.911 |
| 3,816,855 | 6/1974 | Saleh | 3/1.911 |
| 3,958,278 | 5/1976 | Lee et al. | 3/1.911 |
| 4,055,862 | 11/1977 | Farling | 3/1.911 X |
| 4,081,866 | 4/1978 | Upshaw et al. | 3/1.911 |
| 4,094,017 | 6/1978 | Matthews et al. | 3/1.911 |

FOREIGN PATENT DOCUMENTS

| | | | |
|---|---|---|---|
| 2122390 | 1/1973 | Fed. Rep. of Germany | 3/1.911 |
| 2288509 | 5/1976 | France | 3/1.911 |

OTHER PUBLICATIONS

Zimmer Product Encyclopedia, Warsaw Indiana, Jun. 1978, Geo-Patella/Geo-Tibial Total Knee and Multi-Radius Total Knee, pp. A89–A96 and A102–A106.

*Primary Examiner*—Ronald L. Frinks

[57] ABSTRACT

This invention relates to an improved total knee prosthesis of the non-hinged type which advantageously provide normal knee motion and stability during ambulation while substantially obviating loosening or cold flowing of the .ibial component. For this purpose, the total knee prosthesis substantially adopts the anatomical configuration of the natural knee and includes a tibial component comprising condylar bearing members with lower portions completely embedded in tray-shaped elongated sections, in which they are mounted with a predetermined clearance to mechanically absorb part of the natural stresses and torques. The condylar bearing members are also removable and replaceable to obviate any misalignment, natural or not.

6 Claims, 7 Drawing Figures

KNEE PROSTHESIS

The present invention relates to an improved total knee prosthesis of the non-hinged type which advantageously provide normal knee motion including rolling, gliding and axial rotation in both flexion and extension and stability during ambulation.

A large variety of total knee prosthesis has been proposed in the past several years, which may be classified in two major categories, the hinged one and the non-hinged one, respectively.

Up to now the knee prosthesis of the first category have proved to be relatively successful in terms of alleviation of pain and stability during flexion and extension of the knee. However they have also proved to present substantial drawbacks in that they generally involve the removal of the natural ligaments and patella and especially that they only permit motion about a single axis and consequently do not allow for controlled rotation and translation of the knee joint as occur in the human knee. In addition, the hinged type prosthesis generally requires the removal of an important of bone.

The knee prostheses of the second category which may in turn be classified in two sub-categories the unicondylar or "Polycentric" one and the dualcondylar or "Geomedic" one, have permitted to substantially obviate the drawbacks encountered in the hinged type prostheses. Examples of such non-hinged type prosthesis are disclosed in U.S. Pat. Nos. 3,816,855 and 4,081,866 issued on June 18, 1974 and Apr. 4, 1978, in which the respective advantages of the hinged and non-hinged prostheses are clearly emphasized.

However, almost all of the non-hinged type prostheses that are presently known, have also proved to present several common drawbacks.

The most serious one is loosening of the tibial component. Several theories have been advanced to explain this problem and it has been generally concluded that this loosening is due to misalignment of the prosthesis components which leads to an imbalance of the forces transmitted from the femoral component to the tibial component. The asymmetric distribution of load on the plateaues of the tibial component results in local deformation and even shearing of either one or the other plateau and in a rocking movement of the whole tibial component, which results in turn in tibial loosening and failure.

Another drawback commonly reported in plastic deformation (cold flow) of the tibial component when the latter is made of polyethylene, which generally results in subluxation of the femoral component. This deformation of the tibial component is also due to misalignment of the prosthesis components and to the excessive load that the knee must support in some every day activities such as stair climbing.

Further drawbacks specific to each of the different known prosthesis designs have also been reported in the literature. For example, retro-patellar pain has been reported in knee prosthesis with no patello-femoral joint. Lack of inherent stability and development of high contact stresses between plastic and metal surfaces have been reported in knee prosthesis comprising tibial and femoral components with non-conforming articular surfaces to allow for ample axial rotation. On the contrary, improved stability but drastic reduction of the amount of axial rotation have been reported in knee prosthesis comprising tibial and femoral components with conforming articular surfaces.

It is an object of the present invention to provide a structurally improved total knee prosthesis of the non-hinged type, which overcomes most of the above mentioned problems, and more especially tibial loosening and cold flow of the plastics joint, while providing very natural joint physiology.

It is another object of the present invention to provide a total knee prosthesis, which allows for restoration of normal knee motion including rolling, gliding and axial rotation about multi-spatial axes, while allowing for retention of the collateral and cruciate ligaments which lie within the fibrous capsule of the knee and accordingly retention of the intrinsic stability of the human knee, especially during ambulation.

In accordance with the present invention, these objects are achieved with a total knee prosthesis of the non-hinged type, which comprises, in combination, (a) a metallic, dual condylar fermoral component for implantation in the human femur, comprising a lateral condylar element and a medial condylar element integrally connected by a recessed intercondylar element and forwardly and upwardly extended by an integral, substantially trapezoidal patellar articulating element, and (b) a metallic tibial component including two removable, plastics condylar bearing members, for implantation in the human tibia.

The lateral and medial elements of the femoral component are asymmetrical in the longitudinal and tranverse directions and shaped so as to have substantially the same anatomical configuration and divergence as have the human femoral condyles. They are both convex and polycentric with radii of curvature which decrease posteriorly, the medial femoral element being slightly more convex than the lateral one in the anteroposterior direction.

The integral, substantially trapezoidal patellar articulating element includes on its anterior surface, a centrally concaved groove upwardly extending the intercondylar element, for receiving and guiding a natural or prosthesis patellar and stabilizing the same against lateral subluxation.

The tibial component comprises a platform member consisting of two symmetrical spaced apart, elongated sections connected by a bridge section extending from the anterior end of one elongated section to the anterior end of the other to leave an opening in the posterior intercondylar area of the knee. Each elongated section is in the shape of a metal tray with a flat bottom edged by a small vertical rim extending all about the periphery of the flat bottom. Each tray receives and retains one of the condylar bearing member in position with a predetermined clearance.

Each condylar bearing member comprises an upper portion with a slightly concave upper surface allowing for not only rolling and gliding but also rotational motions of the knee due to the asymmetrical shape of the condylar elements of the femoral component sliding thereon, and a lower portion with a flat lower surface.

The lower portion of each condylar bearing member is shaped so as to be completely embedded in its corresponding tray-shaped elongated section and to lie upon the entire bottom surface of the same, to provide protection against cold flow and to improve the stability of the prosthesis. On the other hand, the upper portion is shaped so as to extend over and lie upon the rim of the tray-shaped elongated section, to improve load distribution.

In use, the femoral component is implanted in the patient's femur so as to replace the natural femoral condyles, while the tibial component including the bearing members are implanted in the patient's tibia so as to replace the natural tibial plateaus and menisci respectively. For this purpose, appropriate parts of the patient's bones are surgically removed and replaced by the femoral and tibial components which are disposed one above the other in bearing relationship.

During the operation, the collateral and cruciate ligaments that lie within the fibrous capsule of the patient's knee joint are precautiously preserved. As a matter of fact, the stability of the natural knee and, a fortiori, of the total prosthesis knee according to the invention depends on the retention of these ligaments, the collateral ligaments being responsible for the transverse stability of the knee while the cruciate ligaments provides the anteroposterior stability of the same. Therefore, it is critical that the total knee prosthesis according to the invention which substantially adopts the natural configuration of the human knee which is intrinsically stable, and has the potential for providing natural joint physiology because of the asymmetrical and divergent surfaces of its femoral condylar elements and the slightly concave surfaces of its tibial bearing members which allows for some degree of axial rotation when the knee is flexed, be used together with the natural ligaments of the knee to be stable.

Because of its substantially natural configuration, the knee prosthesis according to the present invention allows for substantial reduction in torque transfer from one component to the other, compared to the known prosthesis, thus reducing loosening of the tibial component while improving metal axial motions of the knee.

Because of the original structure of its tray-shaped tibial platform embedding the lower portions of the condylar bearing members, the knee prosthesis according to the invention also allows for substantial reduction of local deformation of the plateaus (cold flow) and substantial improvement in load distribution compared to the known prosthesis.

Because of the predetermined clearance left between the tray-shaped elongated sections of the tibial component and the bearing members mounted therein, the knee prosthesis according to the invention further allows for absorption of part of the natural stresses and torques to which the knee is submitted, thus also reducing loosening of the tibial component compared to the known prostheses.

At last, because of its bearing members which are removable and therefore replaceable, the prosthesis according to the invention allows for alignment correction during or after the operation.

In accordance with a preferred embodiment of the invention, the lateral and medial condylar, intercondylar and patellar articulating elements together define a U shaped internal recess with orthogonal surfaces to simplify bony resection and implantation on the human femur. Preferably, at least one of the interal orthogonal surface comprises at least one recess for receiving a substantial quantity of gap-filling, surgical cement to provide more positive cement fixation of the femoral component onto the human femur.

In accordance with another preferred embodiment of the invention, each removable condylar bearing members is provided with an interlocking lip which extends forwardly and integrally the lower surface of the lower portion thereof and engages a corresponding recess provided for in the anterior end of the corresponding tray-shaped, elongated section.

In accordance with a further preferred embodiment of the invention, each tray-shaped elongated section is downwardly extended with an integral, centrally located stud to be anchored in the human tibia, to provide better fixation of the tibial component on the human tibia.

The invention will be better understood with reference to the attached drawings wherein.

Figure 1:
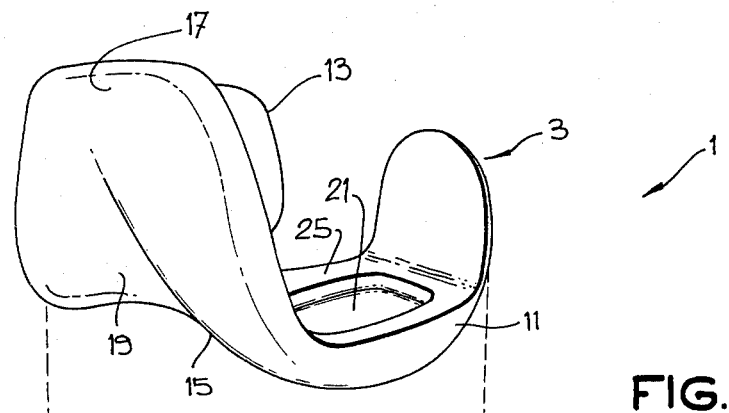
FIG. 1 represents an exploded, perspective view of an embodiment of a total knee prosthesis according to the invention.

The total knee prosthesis 1 shown in an exploded perspective view in FIG. 1 of the drawings, is essentially composed of a dual condylar femoral component 3 and a tibial component 5 including two removable condylar bearing members 7 and 9.

The dual condylar femoral component 3 comprises a lateral condylar element 11 and a medial condylar element 13 which are integrally connected by a recessed intercondylar element 15 and forwardly and upwardly extended by an integral substantially trapezoidal patellar articulating element 17.

To provide the most natural knee motion, the curves of the condylar surfaces of the lateral and medial condylar elements 11 and 13 respectively are not symmetrical either in the longitudinal or transverse directions. On the contrary, they are shaped so that the condylar elements 11 and 13 have substantially the same anatomical configuration and divergence as have the surfaces of the human femoral condyles which are generated from a series of different radii both in the longitudinal and transverse directions.

Such a non-symmetrical shape of the condylar elements, which is new in comparison to what exists in this field, is of a very particular interest since it can be easily understood that only a prosthesis having the same anatomical configuration as the natural knee may provide the patient with a natural knee motion which includes rolling, gliding and axial rotation in either flexion or extension.

As was already emphasized in the preamble of the present disclosure, the ability of providing natural knee motion and stability during ambulation mainly depends on the preservation of ligamentous structures and the shape of the articular surfaces. The preservation of the ligamentous structures can be obtained by a very specific arthroplasty technique with the use of distraction instrumentation such as disclosed in copending application Ser. No. 004,557 filed on Jan. 18, 1979. To obtain the so requested natural knee motion and stability, the femoral condyles must be able to articulate upon the tibial plateaus while being firmly held thereon and the patella must be able to articulate and ride in the central groove of the femur to act as a fulcrum and thus to aid extension of the lower leg.

Such efficient tibio-femoral and patello femoral articulations naturally exist in the human knee and it was a priori obvious to use in total knee arthroplasty prosthetic femoral component having the most natural, disymmetrical shape as is proposed herein, although surprisingly this has never been suggested by the practitioners in the literature, who have been up to now more concerned with pain relief than with restoration of normal knee motion and stability.

Figure 3:
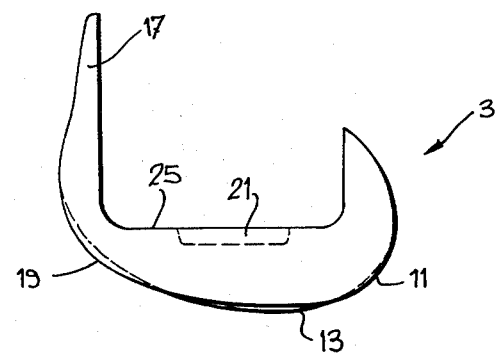
FIG. 3 represents an elevational side view of the femoral component shown in FIG. 2.
Figure 4:
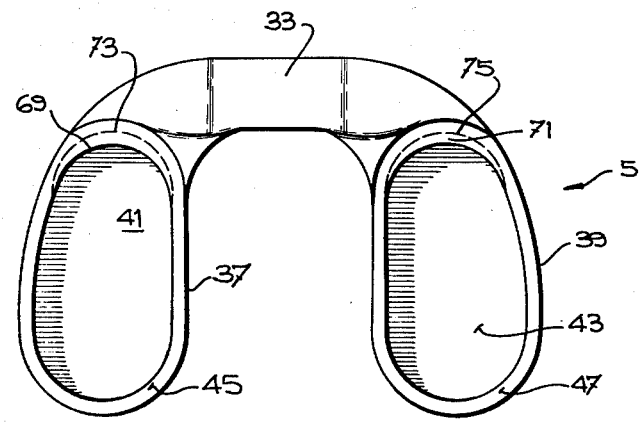
FIG. 4 represents a top plan view of the tibial component of the total knee prosthesis shown in FIG. 1.
Figure 5:
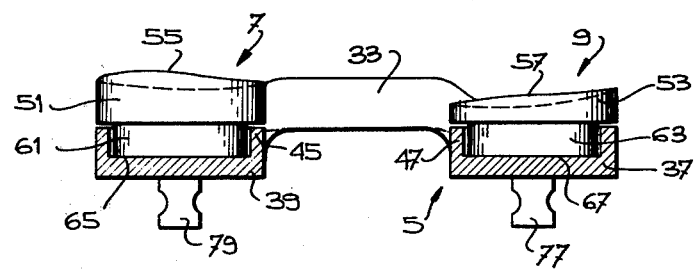
FIG. 5 represents a cross-sectional, rear elevational view of the tibial component shown in FIG. 4.
Figure 6:
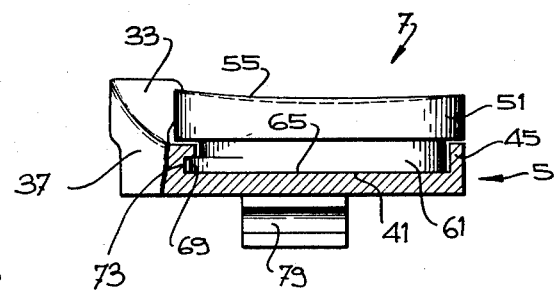
FIG. 6 represents a cross-sectional, side elevational view of the tibial component shown in FIG. 4.

Accordingly, the femoral component 3 comprises lateral and medial condylar elements 11 and 13 having substantially anatomical surfaces which are both convex and polycentric with their radii of curvature which decrease posteriorly. The medial condylar element 13 is slightly more convex than the lateral one in the anterioposterior direction, as can be seen in FIG. 3.

Since the radii of curvature of the condylar elements decrease posteriorly, the laxity of the natural joint is slightly increased, which allows better flexion by rolling and sliding of the condylar elements on the tibial component.

The femoral component 3 also comprises a substantially trapezoidal patellar articulating element 17 with an anatomical anterior surface including a central concaved groove or patellar trochlear 19 extending the recessed intercondylar element 15, for receiving and guiding a natural patella or a prosthesis one. The patella which moves along and comes into contact with this central groove at different areas in the flexion-extension cycle, is advantageously stabilized against lateral subluxation by this groove and by the lateral border of the condylar elements as occurs in the human knee. This substantially favorizes the extension mechanism of the knee while ensuring a good stability to the same.

The femoral component 3 is preferably made of a chromium-cobalt based, steel alloy poured in a mold in the shape of a human femur, and is recessed with orthogonal undersurfaces to simplify bony resection and installation. Such a U-shaped internal shape is already known, as can be seen in U.S. Pat. No. 4,081,866 and its various advantages and possible improvements will not be elaborated, except for the presence of recesses 21 and 23 in the bottom internal surface 25 of the condylar elements 11 and 13 respectively, which may receive a substantial quantity of gap-filling surgical cement, such as methylmethacrylate, and thus provide more positive cement fixation, thus making unnecessary the need of anchoring means, such as studs, fins or the like to be inserted in the femur of the patient.

Referring now to FIGS. 1 and 4 to 6, the tibial component 5 which is used in combination with the above described femoral component 3, comprises a platform member consisting of two spaced apart, elongated sections 37 and 39 connected by a bridge section 33.

The elongated sections 37 and 39 are symmetrical with respect to a vertical plane perpendicular to the bridge section 33 and are both of a substantially ovoidal shape when seen in a top plan view.

The bridge section 33 integrally connects the elongated sections 37 and 39 by their small ends only which are located forwards with respect to the knee, thus leaving an opening in the posterior intercondylar area to allow for retention of cruciate ligaments and of the natural intercondylar eminence which helps provide medial-lateral stability to the knee.

As can be seen in the figures, the bridge section 33 rises slightly above the circumduction plane of the platform member and thus completes the natural intercondylar eminence.

The elongated sections 37 and 39 are both in the shape of metal trays with flat bottoms 41 and 43 edged by a small vertical rims 45 and 47 which extend all about the periphery of the flat bottoms 41 and 43, respectively.

These trays which are preferably made of the same material as the femoral component 3, receive and retain in position with a predetermined clearance two removable condylar bearing members 7 and 9 both made of reinforced plastics material, such as, carbon fiber-reinforced ultrahigh molecular weight polyethylene sold by ZIMMER under the registered trademark POLY-TWO.

The bearing members 7 and 9 each comprises an upper portion 51 or 53 with an upper surface 55 or 57 upon which bears the condylar elements 11 and 13 respectively, and a lower portion 61 or 63 with a flat lower surface 65 or 67.

The peripherical contours and thicknesses of the lower portions 61 and 63 are substantially identical to the internal contours and heights of the rims 45 and 47 of the symmetrical, elongated sections 37 and 39 respectively so that the lower portions 61 and 63 may completely engage the elongated sections 37 and 39, and thus hold the bearing members 7 and 9 onto the same.

The peripherical contours of the upper portions 51 and 53 are substantially identical to the external contours of the rims 45 and 47 of the elongated sections 37 and 39 respectively, on which they lie owing to the thickness of the lower portions 61 and 63 which is identical to the height of the rims 45 and 47.

The upper surfaces 55 and 57 of the bearing members 7 and 9 are substantially symmetrical in shape. They are both shaped so as to be slightly concave as is the surface of the medial tibial plateau in the human knee.

As a matter of fact, in the human knee, the surfaces of the tibial plateaus are non-symmetrical in shape: the surface of the medial tibial plateau is slightly concave whereas the surface of the lateral one is slightly convex. The convexity of the surface of the lateral tibial plateau allows the lateral femoral condyle, which is also different in shape from the medial one, to slide more than the medial condyle as the knee is flexed. This unequal amount of sliding results in the internal rotation of the tibia in flexion and corresponding external rotation in extension.

A priori, it would have been very appropriate to use a prosthesis tibial component having the same anatomical configuration as the human tibial plateaus in combination with the above described femoral component 3 to obtain the best possible results.

However, this has proved not to be possible and convenient because the friction between the metal and/or plastics prosthesis components is not and cannot be identical to that between the natural bones and meniscus.

In so balancing the technical necessities with the anatomical considerations, the slightly concave shape given to the upper surfaces 55 and 57 of the bearing members 7 and 9 have been found to be the most appropriate since this shape ensures sufficient contact between the femoral and tibial components to avoid undesired shifting while allowing for not only rolling and gliding but also rotational motions of the knee, as in the natural knee, due to the asymmetrical convexity of the condylar elements of the femoral component 3 which slide in different amounts on the bearing members and, as a result thereof, rotate the tibial component 5 and consequently the tibia of the patient.

This substantially differs from the general teaching of the literature in which the use of bearing members with very concave surfaces has always been recommended to obtain reliable prosthesis and pain relief.

The original use of bearing members 7 and 9 with slightly concave upper surfaces 55 and 57 and of a femoral component 3 with non symmetrical condylar elements 11 and 13 together with the preservation of the natural ligaments by an appropriate arthroplasty technique, advantageously allows near normal motion of the knee, including external rotation of the tibia in extension, elimination of retropatellar pain when stair climbing and full knee bends. It also reduces the risk of abnormal shearing of the prosthesis components in use since the latter are now able to support the favorize all normal motions of the knee.

As above mentioned, the bearing members 7 and 9 are removably mounted in the tray-shaped, elongated sections 37 and 39 of the tibial component 5. This feature is of a very particular interest since it allows the surgeon who installs the knee prosthesis 1 to obviate misalignment naturally existing in the patient's knee or resulting from faulty sectioning of the patient's bones during fixation the femoral and tibial components 3 and 5, by selection of bearing members of different thicknesses.

The determination of the thickness of each bearing members 7 and 9 can be easily made with a tibial template such as described in copening application Ser. No. 006,073 filed on Jan. 24, 1979 in the name of the same inventor. Advantageously, the bearing members 7 and 9 which have been selected, can be mounted onto the elongated sections 37 and 39 of the tibial component 5 at any time during the operation, thus giving the surgeon more room to work, which may be very useful sometimes.

As also mentioned above, the bearing members 7 and 9 are retained in the tray-shaped, elongated sections 37 and 39 of the tibial component 5 with a predetermined clearance. This clearance is also of a very particular interest because it allows easier introduction of the bearing members 7 and 9 in the elongated sections 37 and 39 and it gives to the tibial component 5 enough mechanical freedom to absorb part of the natural stresses and torques to which the knee is submitted and thus to avoid its loosening from the patient's bone, as often occurs in the known knee prosthesis.

To provide better retainment of the removable bearing members 7 and 9 in the tray-shaped elongated sections 37 and 39, the lower portions 61 and 63 of the bearing members 7 and 9 are each provided with an internal locking lip 69 or 71 forwardly extending from the lower surfaces 65 and 67 respectively and engaging corresponding recesses 73 and 75 provided for in the frontal portions of the sections 37 and 39.

The above described, particular configuration of the condylar bearing members 7 and 9 give the total knee prosthesis 1 three particular advantages when compared to the known prosthesis. First of all, the upper and lower portions of the bearing members 7 and 9 which lie upon the entire bottom surfaces of the tray-shaped, elongated sections 37 and 39 and the upper surfaces of the rims 45 and 47 respectively, substantially facilitate the load distribution. The presence of rims 45 and 47 which completely surround the lower portions of the bearing members 7 and 9 lying on the elongated sections 37 and 39, also provide an extra margin of protection against cold flow of the reinforced plastics material which generally occurs in the most of the known prostheses and substantially affects the intrinsic stability of the knee prosthesis components. The complete embedding of the lower portions of the bearing members 7 and 9 in the tray-shaped, elongated sections 37 and 39, further minimize the possibility of tibial break down due to loosening or buckling up of the bearing members 7 and 9 which also occurs in some of the known prostheses.

The total knee prosthesis 1 is intended for use in patients who are suffering from pain, deformity and/or limited movements due to arthritis of the knee, which cannot be treated by medical means or other established surgical procedures such as synovectomy or high tibial osteotomy, and who have retention of both the collateral and cruciate ligaments.

More especially, the total knee prosthesis 1 can be used in patients suffering from:
   (a) rheumatoid arthritis before a severe irreductible valgus or flexion contracture has developed;
   (b) bicompartmental disease in osteo-arthritis;
   (c) post-traumatic arthritis;
   (d) failed interpositional arthroplasty;
   (e) failed unicompartmental arthroplasty and
   (f) significant patello-femoral pain following tibio-femoral arthroplasty where the cruciate ligaments are preserved.

On the other hand, the total knee prosthesis 1 cannot be used in patients suffering from:
   (a) Arthrodesed knee.
   (b) Paralyzed or otherwise inadequate musculature.
   (c) Previous infectious arthritis.
   (d) Absence of posterior cruciate ligament.
   (e) Severe instability and subluxation secondary to gross loss of integrity of collateral and/or cruciate ligaments.
   (f) Severe fixed or unreducible deformity such as:
      (1) fixed valgum of more than 20 degrees;
      (2) fixed varum of more than 10 degrees;
      (3) fixed flexion of more than 30 degrees.
   (g) Neuopathic knee.

Figure 7:
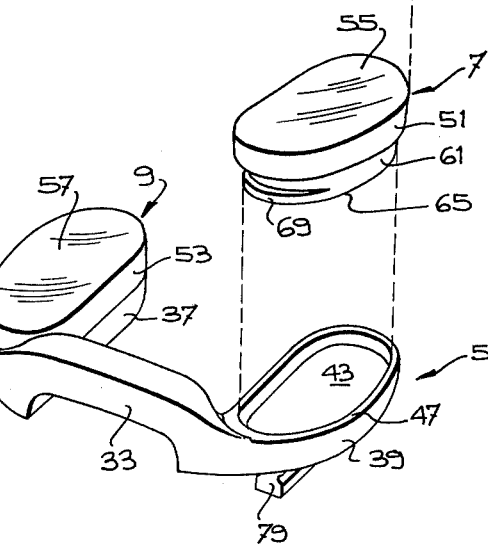
FIG. 7 appearing on the same sheet of drawings as FIG. 1, represents a cross-sectional, side view of a human knee as it would appear after implantation of the total prosthesis knee shown in FIG. 1.
Figure 7:
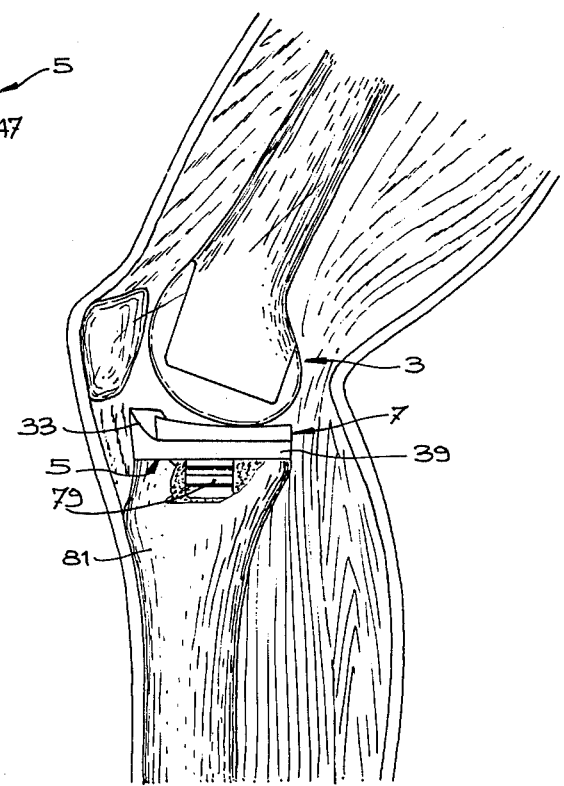
Figure 2:
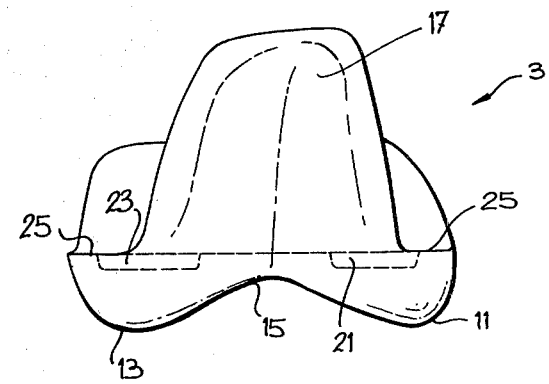
FIG. 2 represents an elevational front view of the femoral component of the total knee prosthesis shown in FIG. 1.

For facilitating and improving implantation of the tibial component 3 in the patient's tibia, the undersides of the elongated sections 37 and 39 are each extended with integral, downwardly directed fixation studs 77 and 79 respectively. As is shown in FIG. 7, the studs 77 and 79 are usually anchored in corresponding resected area in the patient's tibia 81. Preferably, the underside of the elongated sections 37 and 39 and the sides of the studs 77 and 79 are provided with grooves or serrations which may receive a substantial quantity of gap-filling, surgical cement and thus provide a firmer anchoring of the tibial component 5 in the upper end of the patient's tibia 81 after the latter has been suitably prepared.

The total knee prosthesis 1 which substantially adopts the anatomical configuration of the natural knee, has the capability of providing natural knee motion. Because of the shape of its components and its general structure, it obviates most of the complications up to now encountered in total knee arthroplasty, such as loosening of the tibial component due to misalignment of the prosthetic components, retropatellar pain due to the absence of patello femoral joint and impossibility for patients to perform daily activities resulting in the development of high loads in the patello femoral joint, as occurs in stair climbing.

While a prosthesis for a left knee has been shown in the drawings, it is to be understood that a similar femoral component but in the mirror image of the femoral component 3, can be used for a right knee, with an identical tibia component 5.

It is also to be understood that femoral and/or tibia components of different sizes can be used depending on the musculo-skeletal characteristics of the patient.

I claim:

1. A total knee prosthesis of the non-hinged type, comprising in combination:

(a) a metallic, dual condylar femoral component for implantation in the human femur, comprising a lateral condylar element and a medial condylar element integrally connected by a recessed intercondylar element and forwardly and upwardly extended by an integral, substantially trapezoidal patellar articulating element, said lateral and medial elements being asymmetrical in the longitudinal and tranverse directions and shaped so as to have substantially the same anatomical configuration and divergence as have the human femoral condyles, said lateral and medial elements being both convex and polycentric with radii of curvature which decrease posteriorly, said medial femoral element being slightly more convex than said lateral one in the anteroposterior direction, said integral, substantially trapezoidal patellar articulating element including on its anterior surface, a centrally concaved groove upwardly extending the intercondylar element, for receiving and guiding a natural or prothesis patellar and stabilizing the same against lateral subluxation; and (b) a metallic tibial component including two removable, plastics condylar bearing members, for implantation in the human tibia, said tibial component comprising a platform member consisting of two symmetrical, spaced apart, elongated sections connected by a bridge section extending from the anterior end of one elongated section to the anterior end of the other to leave an opening in the posterior intercondylar area of the knee, each elongated section being in the shape of a metal tray with a flat bottom edged by a small vertical rim extending all about the periphery of the flat bottom, each tray receiving and retaining in position with a predetermined clearance, one of the condylar bearing member, each condylar bearing member comprising an upper portion with a slightly concave, upper surface allowing for not only rolling and gliding but also rotational motions of the knee due to the asymmetrical shape of the condylar elements sliding thereof, and a lower portion with a flat lower surface, said lower portion being shaped so as to be completely embedded in the corresponding tray-shaped elongated section and to lie upon the entire bottom surface of the same, to provide protection against cold flow and to improve the stability of the prosthesis, said upper portion being shaped so as to extend over and lie upon the rim of the tray-shaped elongated section to improve load distribution.

2. A total knee prosthesis as claimed in claim 1, wherein said lateral and medial condylar, intercondylar and patellar articulating elements together define a U-shaped internal recess with orthogonal surfaces to simplify bony resection and implantation on the human femur.

3. A total knee prosthesis as claimed in claim 2, wherein at least one of the internal orthogonal surface comprises at least one recess for receiving a substantial quantity of gap-filling, surgical cement to provide more positive cement fixation.

4. A total knee prosthesis as claimed in claim 1, wherein each removable condylar bearing members is provided an interlocking lip which extends forwardly and integrally the lower surface of the lower portion thereof and engages a corresponding recess provided for in the anterior end of the corresponding tray-shaped, elongated section.

5. A total knee prosthesis as claimed in claim 4, wherein each tray-shaped elongated section is downwardly extended with an integral, centrally located stud to be anchored in the human tibia, to provide better fixation of the tibial component on the human tibia.

6. A total knee prosthesis as claimed in claim 1, wherein the upper portions of the condylar bearing members are of different thicknesses.

* * * * *